US009555198B2

(12) United States Patent
Yang et al.

(10) Patent No.: US 9,555,198 B2
(45) Date of Patent: Jan. 31, 2017

(54) AEROSOL GENERATOR INCLUDING MULTI-COMPONENT WICK

(75) Inventors: Zuyin Yang, Midlothian, VA (US);
Susan E. Wrenn, Chesterfield, VA (US); John Wrenn, legal representative, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 1028 days.

(21) Appl. No.: 13/008,563

(22) Filed: Jan. 18, 2011
(Under 37 CFR 1.47)

(65) Prior Publication Data
US 2011/0309157 A1    Dec. 22, 2011

Related U.S. Application Data

(63) Continuation of application No. 12/791,407, filed on Jun. 1, 2010, now abandoned, which is a continuation of application No. 12/576,951, filed on Oct. 9, 2009, now abandoned.

(51) Int. Cl.
| F24F 6/08 | (2006.01) |
| A61M 15/00 | (2006.01) |
| A61M 11/04 | (2006.01) |
| A01M 1/20 | (2006.01) |
| A61L 9/03 | (2006.01) |

(52) U.S. Cl.
CPC .......... *A61M 11/041* (2013.01); *A01M 1/2077* (2013.01); *A61L 9/035* (2013.01); *A61L 9/037* (2013.01); *A61M 11/042* (2014.02); *A61M 15/0003* (2014.02); *A61M 2205/8206* (2013.01)

(58) Field of Classification Search
USPC ........... 392/386, 395–398; 222/146.3, 146.5; 239/1–13
See application file for complete search history.

(56) References Cited

U.S. PATENT DOCUMENTS

| 47,173 | A | * | 4/1865 | Speakman ................... 431/299 |
| 3,695,267 | A | * | 10/1972 | Hirtz et al. .............. 128/203.17 |
| 4,676,237 | A | * | 6/1987 | Wood et al. ............. 128/203.17 |
| 5,388,594 | A | | 2/1995 | Counts et al. |
| 5,647,053 | A | | 7/1997 | Schroeder et al. |
| 6,568,390 | B2 | | 5/2003 | Nichols et al. |

(Continued)

FOREIGN PATENT DOCUMENTS

| GB | 2 449 703 A | 12/2008 |
| GB | 2 450 134 A | 12/2008 |

(Continued)

OTHER PUBLICATIONS

International Preliminary Report on Patentability mailed Apr. 11, 2012 for PCT/EP2010/006198.

(Continued)

*Primary Examiner* — David Angwin
*Assistant Examiner* — Lawrence Samuels
(74) *Attorney, Agent, or Firm* — Buchanan Ingersoll & Rooney PC

(57) ABSTRACT

An aerosol generator includes a composite conduit to transport multiple liquids to a heating element at flow rates such that the liquids arrive at the heating element in desirable concentrations. The heating element volatilizes the liquids to form volatilized fluid, which mixes with ambient air to form an aerosol with desirable concentrations of the multiple liquids.

23 Claims, 3 Drawing Sheets

(56) References Cited

U.S. PATENT DOCUMENTS

| | | |
|---|---|---|
| 6,666,909 B1 | 12/2003 | TeGrotenhuis et al. |
| 6,715,487 B2 | 4/2004 | Nichols et al. |
| 6,869,462 B2 | 3/2005 | TeGrotenhuis et al. |
| 6,875,247 B2 | 4/2005 | TeGrotenhuis et al. |
| 6,899,280 B2 | 5/2005 | Kotary et al. |
| 6,950,607 B2* | 9/2005 | Yip et al. ................ 392/395 |
| 7,007,863 B2* | 3/2006 | Kotary et al. ............ 239/44 |
| 7,055,764 B1* | 6/2006 | Martinez et al. ......... 239/145 |
| 2002/0146242 A1* | 10/2002 | Vieira .................... 392/395 |
| 2002/0181946 A1* | 12/2002 | Brown et al. ............ 392/395 |
| 2003/0168520 A1 | 9/2003 | Triplett et al. |
| 2005/0279854 A1 | 12/2005 | Martens, III et al. |
| 2006/0180143 A1* | 8/2006 | Lind et al. .............. 128/200.14 |
| 2007/0237499 A1* | 10/2007 | DeWitt et al. ........... 392/395 |
| 2007/0262478 A1 | 11/2007 | Price et al. |
| 2008/0017667 A1* | 1/2008 | Valinotti ................. 222/146.3 |
| 2008/0135640 A1* | 6/2008 | Velazquez et al. ....... 239/24 |
| 2009/0020625 A1 | 1/2009 | Trevino |
| 2009/0057437 A1 | 3/2009 | Blondeau et al. |
| 2009/0101729 A1* | 4/2009 | Newman ................. 239/44 |

FOREIGN PATENT DOCUMENTS

| | | |
|---|---|---|
| JP | H11-033097 A | 2/1999 |
| UA | 36768 A | 4/2001 |
| WO | WO 2004/032983 A1 | 4/2004 |
| WO | WO 2006/004902 A1 | 1/2006 |
| WO | 2006086904 A1 | 8/2006 |

OTHER PUBLICATIONS

International Search Report and Written Opinion mailed Dec. 20, 2010 for International Application No. PCT/EP2010/006198.

Japanese Official Action issued Aug. 4, 2014 for Japanese Appln. No. 2012-532499.

Notice of Allowance dated Dec. 9, 2014 for Ukrainian Patent Appln. No. 201205053.

European Office Action issued Jun. 28, 2016 in corresponding European Patent Application No. 10774131.6 (5 pages).

Utada et al., "Monodisperse Double Emulsions Generated From A Microcapillary Device", www.sciencemag.org, Science, vol. 308, Apr. 22, 2005, pp. 537-541.

* cited by examiner

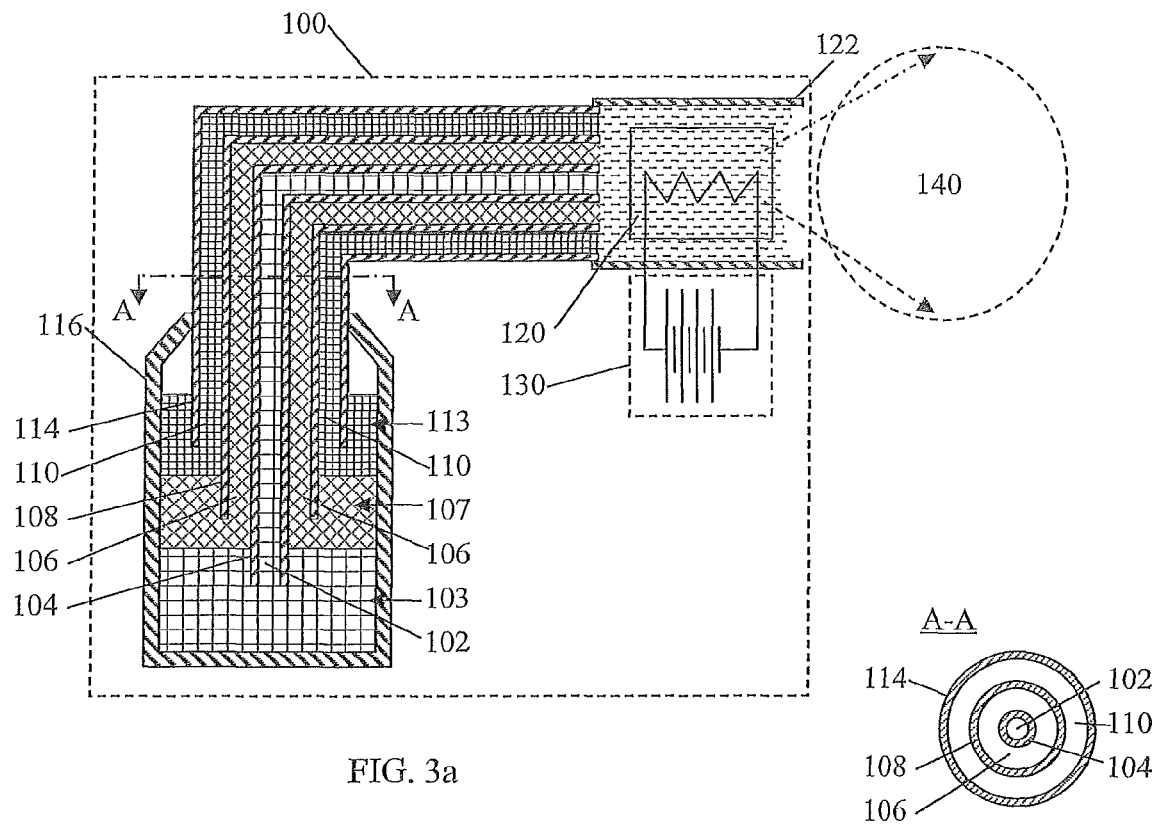
FIG. 3a
FIG. 3b
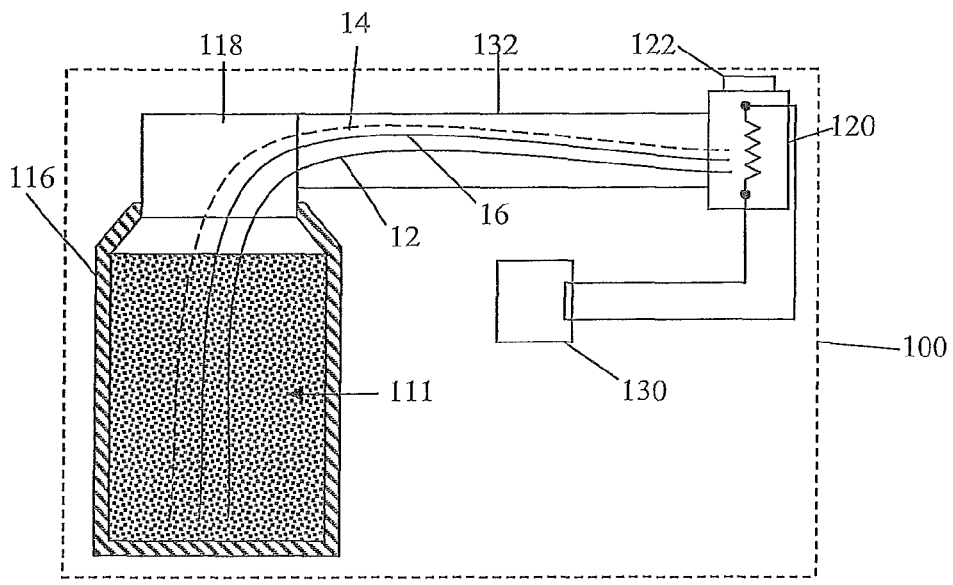
FIG. 4

AEROSOL GENERATOR INCLUDING MULTI-COMPONENT WICK

CROSS REFERENCE TO RELATED APPLICATION

This application is a continuation application of U.S. application Ser. No. 12/791,407 entitled AEROSOL GENERATOR INCLUDING MULTI-COMPONENT WICK, filed Jun. 1, 2010 now abandoned, which is a continuation application of U.S. Application No. 12/576,951 entitled AERODOL GENERATOR INCLUDING MULTI-COMPONENT WICK, filed on Oct. 9, 2009 now abandoned, the entire content of which is hereby incorporated by reference.

SUMMARY

Provided is an aerosol generator including a composite conduit to transport multiple liquids to a heating element such that the liquids arrive at the heating element in desirable concentrations. The heating element is operable to volatilize the liquids to form volatilized fluid, which mixes with ambient air to form an aerosol with desirable concentrations of the multiple liquids.

Also provided is a method of generating an aerosol comprising transporting first and second liquids through first and second wicks from at least one liquid supply to a heating element at rates such that the liquids are present at the heating element in desirable concentrations and volatilizing the liquids at the heating element to form volatilized fluid, which mixes with ambient air to form an aerosol with desirable concentrations of the liquids.

BRIEF DESCRIPTION OF THE DRAWINGS

FIG. 1a is a side view of the arrangement and FIG. 1b is a cross-sectional view of the arrangement.

FIG. 3a shows a schematic of another embodiment of an aerosol generator having a composite conduit with multiple passages.

FIG. 3b shows a cross section of the composite conduit shown in FIG. 3a.

FIG. 4 shows a schematic of still another embodiment of an aerosol generator having a composite conduit with multiple passages.

DETAILED DESCRIPTION OF PREFERRED EMBODIMENTS

Figure 1B:
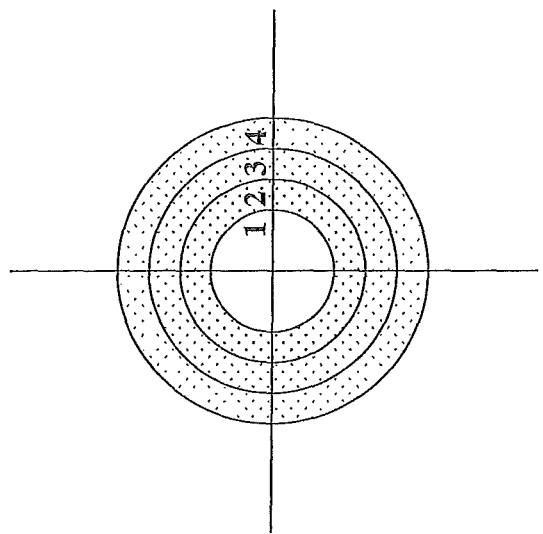
FIGS. 1a and 1b are schematics of an embodiment of an arrangement containing plural layers of wicking materials for transporting a multi phase solution. Specifically.

Provided is a device for generation of an aerosol. The device may be used for various purposes such as generating flavored aerosols, scented aerosols, or the like. The device volatilizes liquid material, which optionally condenses in ambient air to form an aerosol.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. For aerosols intended for human inhalation, a mass median particle diameter of particles of the aerosol less than 2 microns, preferably between 0.2 and 2 microns, and more preferably between 0.5 and 1 micron, is preferred.

Aerosols and the precursor vapor may also have applications in creating nano particles and other powders. The volatilization of metal containing liquids brings the possibility of producing micro ball bearings, foam metal and metal plating in a precise and cost effective manner. The uses of aerosols and the precursor vapor also have applications in the area of lubrication, where disbursement of the lubricant may be facilitated with the introduction of a concentration of particles of lubricant.

In a preferred embodiment, the device includes a composite conduit having plural passages which transport liquids to form an aerosol. The passages can be capillary tubes, wicks, wicks of various wicking material or a combination thereof. More specifically, the composite conduit can be used to transport liquids from at least one liquid supply to a heating element at rates such that the liquids are present at the heating element in desirable concentrations. The heating element volatilizes the liquids to form volatilized fluid, which mixes with ambient air to form an aerosol with desirable concentrations of the liquids.

As used herein, "desirable concentrations" refer to concentrations that will produce an aerosol with preferred characteristics, which is dependent upon the composition of the liquids that are volatized to form the aerosol. Accordingly, the ratio and amounts of the liquids transported to the heating element determines the composition of the aerosol formed.

In a preferred embodiment, the ratio and amounts of the liquids transported to the heating element may be controlled through selection of the passages (capillary tubes, wicks, wick material) and liquids. Preferably, two or more liquids are transported and the liquids preferably are immiscible in each other. If stored together in a single liquid supply, the immiscible liquids may form multiple phases. The wicks operate by capillary action and may be combined with one or more capillary tubes. In an example, two or more wicks and a capillary tube would be adapted to transport a plurality of liquids. Preferably, wicks contain numerous pores, which act as capillaries and cause the liquid to be drawn into them. Wicks may be selected based on their wettability for an immiscible liquid or phase. The capillary tube preferably has an internal diameter of 0.1 to 10 mm, preferably 0.5 to 1 mm, more preferable about 0.1 to 0.5 mm, and even more preferably about 0.15 mm, corresponding to internal cross sectional areas of 8×10-5 to 80 mm$^2$, 0.002 to 0.8 mm$^2$, 0.008 to 0.2 mm$^2$, and about 0.02 mm$^2$, respectively. The dimensions of the capillaries and/or wicks are further factors that affect the amounts of liquids transported to the heating element.

Various geometries can be used for transporting the liquids at desired flow rates to the heating element. For example, multiple wicking materials, such as, for example, one or more synthetic fibers and cotton, may be combined to form a woven wick to transport one or more liquids. In an embodiment, wicking materials may be arranged in a concentric pattern around a central capillary tube, such as two or more tubes of wicking materials arranged in a concentric pattern around a central capillary tube. The wicking materials may be separated by wire mesh, which may also act as a wicking material for liquid transport.

Figure 1A:
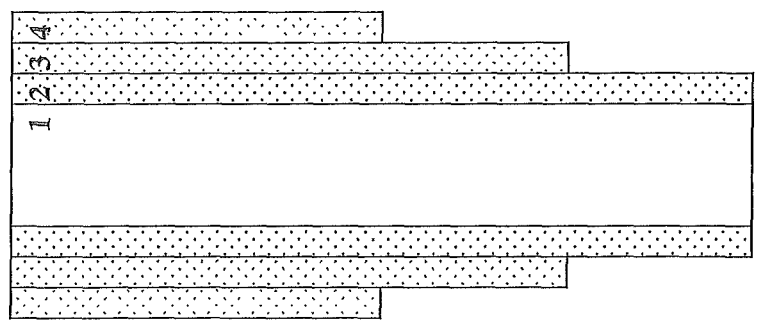

FIGS. 1a and 1b are schematics of an arrangement containing three layers of wicking materials for transporting a three phase solution. Specifically, FIG. 1a is a side view of a coaxial arrangement and FIG. 1b is a cross-sectional view of the arrangement. In particular, a capillary tube 1 is concentrically surrounded by three layers 2, 3, 4 of wicking materials. It is furthermore possible for a four phase solution to be transported, with the capillary tube 1 transporting one phase and the three layers 2, 3, 4 of wicking materials transporting three other phases. If desired, the capillary tube and/or the fourth wick can be omitted.

The immiscible liquid may comprise one or more hydrophobic liquids (e.g., one or more essential oils) and one or more hydrophilic liquids (e.g., propylene glycol, glycerol and/or other aerosol former). In a reservoir containing a multiphase liquid, the phases may separate into discrete layers with lower density phases forming over higher density phases. An arrangement for transporting immiscible liquids may comprise passages having different lengths adapted to be in contact with different layers of the multiphase liquid. In the case of a two phase immiscible liquid comprising a lighter flavor-rich phase and a heavier aerosol former phase, first and second wicks or capillary tubes for transporting the immiscible liquids may comprise a shorter wick or shorter capillary tube adapted to be in contact with the lighter flavor-rich liquid and a longer wick or longer capillary tube adapted to be in contact with the heavier aerosol former. Further, if the first and second wicks/capillary tubes for transporting the immiscible liquids are arranged in a concentric pattern, the shorter wick/capillary tube adapted to be in contact with the lighter flavor-rich liquid may surround the longer wick/capillary tube adapted to be in contact with the heavier aerosol former.

Thus, an aerosol generator can comprise an arrangement for transporting immiscible liquids from at least one liquid supply to a heating element at rates such that the liquids are present at the heating element in desirable concentrations. The heating element volatilizes the immiscible liquids to form volatilized fluid, which mixes with ambient air to form an aerosol with desirable concentrations of the immiscible liquids.

The heating element may comprise a wire mesh heater embedded in a downstream end of the wicks. The heating element may be a stainless steel wire mesh or a stainless steel serpentine strip. The heating element is connected to a power supply, which can be a portable power supply such as a direct current battery. However, the use of alternating current may also be effective. When the aerosol generator comprises one or more capillary tubes, the heating element is operable to volatilize the liquid(s) transported via the capillary tube(s) at the downstream end of the capillary tube(s), similar to the volatilization of the liquids transported via the wicks at the downstream end of the wicks.

The immiscible liquids preferably comprise multiple phases, which are transported from one liquid supply. However, the liquids can be supplied from different liquid supplies if desired. The immiscible liquids may comprise at least one hydrophobic liquid and at least one hydrophilic liquid such as a flavor system and aerosol former. The flavor system may comprise one or more essential oils. The aerosol former may comprise propylene glycol, glycerol, or mixtures thereof.

Figure 2:
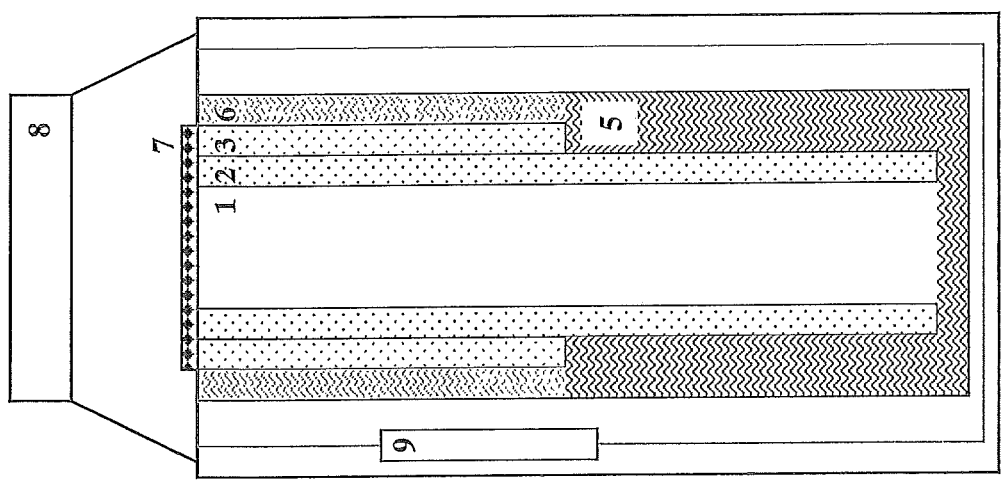
FIG. 2 is a schematic of an embodiment of an aerosol generator for generating an aerosol from two immiscible liquids that comprise two phases.

FIG. 2 is a schematic of an aerosol generator for generating an aerosol from two immiscible liquids that comprise two phases. A capillary tube 1 is concentrically surrounded by two layers 2, 3 of wicking materials, which transport liquids 5, 6, respectively, to the heating element 7. After the heating element 7 volatilizes the immiscible liquids to form volatilized fluid, the volatilized fluid may be transferred to a mouthpiece 8, from which formed aerosol may be inhaled. A control circuit 9 regulates the supply of power, preferably direct current, to the heating element 7. If desired, an additional phase may to be transported through the capillary tube 1.

FIG. 3a is a schematic of another embodiment of an aerosol generator 100 for generating an aerosol from three immiscible liquids that comprise three phases. A reservoir 116 of the aerosol generator 100 is filled with the three liquids. A first capillary tube 104 is concentrically surrounded by second and third capillary tubes 108 and 114. First capillary tube 104 transports first liquid 103 which may be a hydrophilic liquid, to the heating element 120 from the reservoir 116. Second and third capillary tubes 108 and 114 transport second and third liquids 107 and 113, which may be neutral and hydrophobic liquids, respectively, to the heating element 120. After the heating element 120 volatilizes the immiscible liquids to form volatilized fluid, the volatilized fluid may be transferred to a mouthpiece 122, from which formed aerosol 140 may be inhaled. A control circuit 130 regulates the supply of power, preferably direct current, to the heating element 120.

The concentric capillary tubes 104/108/114 form a composite conduit of the aerosol generator 100. FIG. 3b shows a cross section of the composite conduit of FIG. 3a at AA. As shown in FIG. 3b, when concentric capillary tubes are used, the distance between capillary sidewalls is comparable to the inner diameter of the center capillary tube as mentioned previously. For example, the distance between 104 and 108 or 108 and 110 in FIG. 3b. can be 0.1 to 10 mm, preferably 0.5 to 1 mm, more preferable about 0.1 to 0.5 mm, and even more preferably about 0.15 mm. Preferably, the capillary tube can be glass, porous metal, synthetic material and combinations thereof.

FIG. 4 is a schematic of another embodiment of an aerosol generator 100 for generating an aerosol from three immiscible liquids that comprise three phases. A first wick 12 transports a first phase which may be a hydrophilic liquid, of a liquid 111 to the heating element 120 from a reservoir 116. In this embodiment, liquid 111 can be an emulsion of immiscible liquids (e.g., a hydrophilic liquid, a hydrophobic liquid and a neutral liquid or a combination of any two thereof). Second and third wicks 14 and 16 transport additional phases which may be neutral and hydrophobic liquids, respectively, of liquid 111 to the heating element 120. As shown in FIG. 4, the first, second and third wicks 12/14/16 may transport the liquids through a cap 118 of the reservoir 116 and through a passage 132 or the like, to the heating element 120. After the heating element 120 volatilizes the immiscible liquids to form volatilized fluid, the volatilized fluid may be transferred to a mouthpiece 122, as described previously. A control circuit 130 regulates the supply of power to the heating element 120, also as described previously.

In a preferred embodiment, first, second and third wicks 12/14/16 may be interwoven (e.g., braided) or separate. Interwoven wicks can be of various materials to transport the various phases. For example, synthetic wick materials to transport the hydrophilic phase can include plastic or rubber molecules with OH groups having an affinity for the polar phase liquids. Non-polar plastic material without OH group constituents have an affinity for the non-polar phase liquid and natural materials such as cotton have an affinity for the neutral phase liquid. As such, first second and third wicks 12/14/16 can transport separate phases from liquid 111 to the heating element 120 such that the phases are present at the heating element in desirable concentrations.

Also provided is a method of generating an aerosol comprising transporting immiscible liquids from at least one liquid supply to a heating element at rates such that the liquids are present at the heating element in desirable concentrations and volatilizing the immiscible liquids at the heating element to form volatilized fluid, which mixes with ambient air to form an aerosol with desirable concentrations of the immiscible liquids.

While various embodiments have been described, it is to be understood that variations and modifications may be resorted to as will be apparent to those skilled in the art. Such variations and modifications are to be considered within the purview and scope of the claims appended hereto.

What is claimed is:

1. An aerosol generator comprising:
   a reservoir configured to hold multiple liquids, wherein the multiple liquids are separated into discrete layers with lower density liquids forming over higher density liquids;
   a heating element operable to volatilize the multiple liquids to form a volatilized fluid, which mixes with ambient air to form an aerosol;
   a composite conduit to transport the multiple liquids to the heating element, wherein the composite conduit includes a first capillary tube, which is concentrically surrounded by second and third capillary tubes, and wherein the first, second, and third capillary tubes have different lengths adapted to be in contact with a different liquid within the multiple liquids; and
   a mouthpiece configured to receive the aerosol, from which the aerosol may be inhaled.

2. An aerosol generator comprising:
   a reservoir configured to hold an emulsion of immiscible liquids;
   a heating element operable to volatilize the emulsion of immiscible liquids to form a volatilized fluid, which mixes with ambient air to form an aerosol;
   a first wick operable to transport a first liquid, a second wick operable to transport a second liquid, and a third wick operable to transport a third liquid from the emulsion of immiscible liquids to the heating element; and
   a mouthpiece configured to receive the aerosol, from which the aerosol can be inhaled.

3. The aerosol generator of claim 2, wherein the first, second, and third capillary wicks are different lengths.

4. The aerosol generator of claim 2, wherein the first, second, and third wicks are arranged in a concentric pattern or interwoven pattern.

5. The aerosol generator of claim 2, wherein the emulsion of immiscible liquids comprise one or more hydrophobic liquids and one or more hydrophilic liquids.

6. The aerosol generator of claim 1, wherein the liquids comprise first, second, and third liquids that are immiscible in each other and are located in a single liquid supply.

7. The aerosol generator of claim 1, wherein the liquids comprise at least one hydrophobic liquid and at least one hydrophilic liquid.

8. The aerosol generator of claim 1, wherein the liquids comprise a flavor system and an aerosol former.

9. The aerosol generator of claim 8, wherein the flavor system comprises one or more essential oils.

10. The aerosol generator of claim 8, wherein the aerosol former comprises a material selected from the group consisting of propylene glycol, glycerol, and mixtures thereof.

11. A method of generating an aerosol comprising:
    transporting first, second, and third liquids through first, second, and third wicks from at least one liquid supply holding an emulsion of immiscible liquids to a heating element; and
    volatilizing the liquids at the heating element to form volatilized fluid, which mixes with ambient air to form an aerosol.

12. The method of claim 11, wherein the first, second, and third wicks are different lengths.

13. The method of claim 11, wherein the liquids comprise at least one hydrophobic liquid and at least one hydrophilic liquid.

14. The method of claim 11, wherein the liquids comprise a flavor system and aerosol former.

15. The method of claim 14, wherein the flavor system comprises one or more essential oils.

16. The method of claim 14, wherein the aerosol former comprises a material selected from the group consisting of propylene glycol, glycerol, and mixtures thereof.

17. The method of claim 11, further comprising a third wick operable to transport a third liquid to the heating element.

18. The aerosol generator of claim 1, wherein the first capillary tube transports a hydrophilic liquid, the second capillary tube transports a hydrophilic or a hydrophobic liquid, and the third capillary tube transports a hydrophobic liquid, respectively, to the heating element.

19. The aerosol generator of claim 2, wherein the first wick transports a hydrophilic liquid, the second wick transports a hydrophilic or a hydrophobic liquid, and the third wick transports a hydrophobic liquid, respectively, to the heating element.

20. A method of generating an aerosol comprising:
    separating multiple liquids into discrete layers with lower density liquids forming over higher density liquids, wherein the multiple liquids comprises first, second, and third liquids that are immiscible in each other and are located in a single liquid supply;
    transporting the multiple liquids from the single liquid supply through first, second, and third capillary tubes to a heating element; and
    volatilizing the liquids at the heating element to form volatilized fluid, which mixes with ambient air to form an aerosol.

21. The method of claim 20, wherein the first, second, and third capillary tubes are different lengths.

22. The method of claim 20, wherein the liquids comprise at least one hydrophobic liquid and at least one hydrophilic liquid.

23. An aerosol generator comprising:
    a reservoir configured to hold two or more liquids, wherein the two or more liquids are separated into discrete layers with lower density liquids forming over higher density liquids;
    a heating element operable to volatilize the multiple liquids to form a volatilized fluid, which mixes with ambient air to form an aerosol;
    a composite conduit to transport the two or more multiple liquids to the heating element, wherein the composite conduit includes an inner capillary tube, which is concentrically surrounded by one or more outer capillary tubes, and wherein the inner capillary tube and the one or more outer capillary tubes have different lengths adapted to be in contact with a different liquid within the multiple liquids; and
    a mouthpiece configured to receive the aerosol, from which the aerosol may be inhaled.

* * * * *